United States Patent [19]
Caldwell et al.

[11] 3,931,162
[45] Jan. 6, 1976

[54] N-AMINOMETHYL HETEROCYCLIC THIOACETAMIDES

[75] Inventors: Henry C. Caldwell, Ambler; Bernard Loev, Broomall, both of Pa.

[73] Assignee: SmithKline Corporation, Philadelphia, Pa.

[22] Filed: Dec. 3, 1974

[21] Appl. No.: 529,210

Related U.S. Application Data

[60] Division of Ser. No. 266,181, June 26, 1972, which is a continuation-in-part of Ser. No. 220,418, Jan. 24, 1972, abandoned.

[52] U.S. Cl.... 260/247.1 M; 260/283 S; 260/287 R; 260/288 R; 424/248; 424/258
[51] Int. Cl.² .............. C07D 295/12; C07D 215/12
[58] Field of Search..... 260/283 S, 247.1 M, 288 R, 260/287 R

[56] References Cited
UNITED STATES PATENTS

| | | |
|---|---|---|
| 3,573,304 | 3/1974 | Eberle et al.................. 260/288 R |
| 3,726,878 | 4/1973 | Kanai et al. ...................... 260/283 S |
| 3,749,728 | 7/1973 | Loev................................ 260/283 S |
| 3,825,547 | 7/1974 | Loev................................ 260/283 S |
| 3,853,865 | 12/1974 | Brenner et al.................. 260/283 S |
| 3,876,645 | 4/1975 | Kanai et al. ...................... 260/283 S |
| 3,880,860 | 4/1975 | Loev................................ 260/283 S |
| 3,882,126 | 5/1975 | Brenner et al.................. 260/283 S |

*Primary Examiner*—Raymond V. Rush
*Assistant Examiner*—Mary C. Vaughn
*Attorney, Agent, or Firm*—Joan S. Keps; Richard D. Foggio; William H. Edgerton

[57] ABSTRACT

N-Aminomethyl heterocyclic thioacetamide compounds are prepared by reacting a heterocyclic thioacetamide with formaldehyde and an amine. The products inhibit gastric acid secretion.

5 Claims, No Drawings

N-AMINOMETHYL HETEROCYCLIC THIOACETAMIDES

This is a division of application Ser. No. 266,181 filed June 26, 1972, which is a continuation-in-part of Ser. No. 220,418, filed Jan. 24, 1972 now abandoned.

This invention relates to new N-aminomethyl heterocyclic thioacetamide compounds having pharmacodynamic activity. In particular, these compounds inhibit gastric acid secretion.

The compounds of this invention are represented by the following formula:

FORMULA I

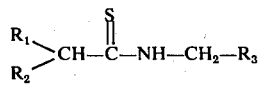

in which:
- $R_1$ is 2-pyridyl, 2-pyrimidyl, 4-pyrimidyl, 2-pyrazinyl, 2-pyrrolyl, 2-quinolyl, 2-thiazolyl or 4-thiazolyl;
- $R_2$ is hydrogen, lower alkyl, lower alkenyl or $-(CH_2)_n$-phenyl;
- $R_3$ is di-lower alkylamine, N-lower alkyl-N-phenylamine, pyrrolidino, piperidino morpholino or N-lower alkylpiperazino and $n$ is 0 or 1.

This invention also includes pharmaceutically acceptable acid addition salts of the compounds of Formula I.

The pharmacologically active compounds of this invention have the basic structure of Formula I. However, it is apparent to one skilled in the art that well known nuclear substituents such as lower alkyl, lower alkoxy or halogen may be incorporated on the heterocyclic rings of $R_1$ and the phenyl rings. These substituted compounds are used as are the parent compounds.

Preferred compounds of this invention are represented by Formula I above in which $R_2$ is hydrogen or lower alkyl and $R_3$ is di-lower alkylamino, pyrrolidino, piperidino or morpholino.

Advantageous compounds of this invention are represented by Formula I in which $R_1$ is 2-pyridyl, $R_2$ is lower alkyl and $R_3$ is diethylamino, pyrrolidino or morpholino.

Most preferably, in the compounds of Formula I, $R_1$ is 2-pyridyl.

Particularly advantageous compounds of this invention are represented by Formula I in which $R_1$ is 2-pyridyl, $R_2$ is methyl, ethyl or isopropyl and $R_3$ is diethylamino, pyrrolidino or morpholino. Included in this group are 3-methyl-N-morpholinomethyl-2-(2-pyridyl)thiobutanamide, N-morpholinomethyl-2-(2-pyridyl)thiopropanamide, 3-methyl-N-pyrrolidinomethyl-2-(2-pyridyl)thiobutanamide and N-diethylaminomethyl-3-methyl-2-(2-pyridyl)thiobutanamide.

The compounds of this invention produce inhibition of gastric acid secretion. This activity is demonstrated by administration to pylorus ligated rats at doses of about 10 to about 50 gm./kg. orally. Also, this activity is demonstrated by administration to chronic gastric fistula rats (Brodie et al., Amer. J. Physiol. 202:812-814, 1962) at doses of about 50 mg./kg. orally. In these procedures, compounds which produce an increase in gastric pH or a decrease in the volume of gastric juice or both are considered active.

These compounds show antiulcer activity in the restraint-stress method in which an oral administration to rats these compounds inhibit the development of experimental ulcers.

The compounds of this invention are prepared as follows:

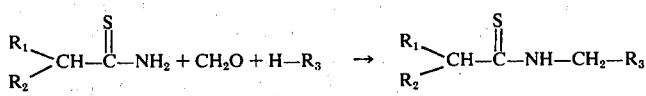

The terms $R_1$-$R_3$ are as defined above.

According to the above procedure, a heterocyclic thioacetamide is reacted with formaldehyde and an amine. The reaction is preferably carried out in an organic solvent, such as a lower alkanol, for example methanol. The reaction is carried out, for example, at about $-40°C$. to about $90°C$., preferably at the lower temperatures when $R_2$ is hydrogen.

The heterocyclic thioacetamide starting materials are known to the art or are prepared, for example, by reacting the corresponding substituted acetonitrile ($R_1R_2CH$-$CN$) with hydrogen sulfide in the presence of base such as an amine or by reacting with ammonium polysulfide. The substituted acetonitriles may be prepared from substituted ketones or carboxaldehydes ($R_1R_2C=O$) by reducing to the corresponding alcohol using a reducing agent such as sodium borohydride, then treating the alcohol with a chlorinating agent such as thionyl chloride and treating the resulting chloride with an alkali metal cyanide such as sodium or potassium cyanide.

The pharmaceutically acceptable acid addition salts of the compounds of Formula I are formed with organic and inorganic acids by methods known to the art. For example, the base is reacted with an organic or inorganic acid in aqueous miscible solvent, such as acetone or ethanol, with isolation of the salt by concentration and cooling or in aqueous immiscible solvent, such as ethyl ether or chloroform, with the desired salt separating directly. Exemplary of the salts which are included in this invention are maleate, fumarate, succinate, oxalate, benzoate, methanesulfonate, ethanedisulfonate, benzenesulfonate, acetate, propionate, tartrate, citrate, hydrochloride, hydrobromide, sulfate, sulfamate, phosphate and nitrate salts.

The compounds of this invention are administered internally either parenterally, rectally or, preferably, orally in an amount to produce the desired biological activity.

Preferably, the compounds are administered in conventional dosage forms prepared by combining an appropriate dose of the compound with standard pharmaceutical carriers.

The pharmaceutical carrier may be for example a solid or a liquid. Exemplary of solid carriers are lactose, magnesium stearate, cerra alba, sucrose, talc, stearic acid, gelatin, agar, pectin, acacia or cocoa butter. The amount of solid carrier will vary widely but preferably will be from about 25 mg. to about 1 gm. Exemplary of liquid carriers are syrup, peanut oil, olive oil, sesame oil, propylene glycol, polyethylene glycol (mol. wt. 200–400) and water. The carrier or diluent may include a time delay material well known to the art such as, for example, glyceryl monostearate or glyceryl distearate alone or with a wax.

A wide variety of pharmaceutical forms can be employed, for example the preparation may take the form of tablets, capsules, powders, suppositories, troches, lozenges, syrups, emulsions, sterile injectable liquids or liquid suspensions or solutions.

The pharmaceutical compositions are prepared by conventional techniques involving procedures such as mixing, granulating and compressing or dissolving the ingredients as appropriate to the desired preparation.

The terms "lower alkyl" and "lower alkoxy" where used herein denote groups having 1–6, preferably 1–4, carbon atoms; "lower alkenyl" denotes groups having 2–6, preferably 2–4, carbon atoms and "halogen" denotes chloro, bromo or fluoro.

The following examples are not limiting but are illustrative of the compounds of this invention and processes for their preparation.

EXAMPLE 1

To a solution of 1.0 g. of 3-methyl-2-(2-pyridyl)thiobutanamide in 20 ml. of methanol is added, at one time, 0.45 g. of morpholine and 0.42 ml. of a 37 percent formalin solution. The reaction is stirred for 15 hours at 25°C., then refluxed on a steam bath for 20 minutes. The solvents are evaporated in vacuo and the residue is distilled to give 3-methyl-N-morpholinomethyl-2-(2-pyridyl)thiobutanamide, b.p. 110 –112°C. (0.005 mm.).

EXAMPLE 2

2-Phenyl-(2-(2-pyridyl)thioacetamide (1.14 g.) is suspended in 20 ml. of methanol. To the suspension is added 0.49 ml. of morpholine and 0.45 ml. of formalin. The mixture is heated on a steam bath until all of the materials are dissolved. The solution is then cooled and hexane is added. Concentrating to dryness and recrystallizing the residue from isopropanol gives N-morpholinomethyl-2-phenyl-2-(2-pyridyl)thioacetamide, m.p. 128°–130°C.

EXAMPLE 3

By the procedure of Example 1, using the following thioamides in place of 3-methyl-2-(2-pyridyl)thiobutanamide:
  2-(2-pyridyl)thiobutanamide
  2-(2-pyridyl)thiopentanamide
  2-(2-pyridyl)thiohexanamide
  2-(2-pyridyl)thiooctanamide
the products are respectively:
  N-morpholinomethyl-2-(2-pyridyl)thiobutanamide
  N-morpholinomethyl-2-(2-pyridyl)thiopentanamide
  N-morpholinomethyl-2-(2-pyridyl)thiohexanamide
  N-morpholinomethyl-2-(2-pyridyl)thiooctanamide.

EXAMPLE 4

Using 2-(2-pyridyl)-4-thiopentenamide in place of 3-methyl-2-(2-pyridyl)thiobutanamide in the procedure of Example 1, the product is N-morpholinomethyl-2-(2-pyridyl)-4-thiopentenamide.

EXAMPLE 5

To a solution of 2.0 g. (0.013 m.) of 2-(2-pyridyl)thioacetamide in 30 ml. of methanol at −40°C. is added 1.15 g. (0.013 m.) of morpholine in 6 ml. of methanol and 1.05 ml. of a 37 percent formalin solution (0.013 m.) in 6 ml. of methanol. The solution is allowed to warm up to −20°C. and kept at this temperature for 48 hours.

The solution is concentrated in vacuo and the residue is deposited on silica gel and chromatographed on a 20 inch × 1.5 inch dry column, using ethyl acetate as the eluant. The product fraction is evaporated and the residue is distilled in vacuo to give N-morpholinomethyl-2-(2-pyridyl)thioacetamide.

EXAMPLE 6

By the procedure of Example 5, using the following thioamides in place of 2-(2-pyridyl)thioacetamide:
  2-(2-pyrazinyl)thioacetamide
  2-(2-quinolyl)thioacetamide
  2-(2-pyrrolyl)thioacetamide
  2-(6-methyl-2-pyridyl)thioacetamide
  2-(5-methyl-2-pyridyl)thioacetamide
  2-(4-methyl-2-pyridyl)thioacetamide
  2-(3-methyl-2-pyridyl)thioacetamide
  2-(5-ethyl-2-pyridyl)thioacetamide
  2-(4-methoxy-2-pyridyl)thioacetamide
  2-(4-ethoxy-2-pyridyl)thioacetamide
the products are, respectively:
  N-morpholinomethyl-2-(2-pyrazinyl)thioacetamide
  N-morpholinomethyl-2-(2-quinolyl)thioacetamide
  N-morpholinomethyl-2-(2-pyrrolyl)thioacetamide
  2-(6-methyl-2-pyridyl)-N-morpholinomethyl-thioacetamide
  2-(5-methyl-2-pyridyl)-N-morpholinomethyl-thioacetamide
  2-(4-methyl-2-pyridyl)-N-morpholinomethyl-thioacetamide
  2-(3-methyl-2-pyridyl)-N-morpholinomethyl-thioacetamide
  2-(5-ethyl-2-pyridyl)-N-morpholinomethyl-thioacetamide
  2-(4-methoxy-2-pyridyl)-N-morpholinomethyl-thioacetamide
  2-(4-ethoxy-2-pyridyl)-N-morpholinomethyl-thioacetamide.

EXAMPLE 7

By the procedure of Example 1, using the following thioamides in place of 3-methyl-2-(2-pyridyl)thiobutanamide:
  2-(2-pyrazinyl)thiobutanamide
  2-phenyl-2-(2-pyrazinyl)thioacetamide
  2-(4-chlorophenyl)-2-(2-pyrimidyl)thioacetamide
  2-phenyl-2-(2-thiazolyl)thioacetamide
  2-(4,6-dimethyl-2-pyrimidyl)thioacetamide
the products are, respectively:
  N-morpholinomethyl-2-(2-pyrazinyl)thiobutanamide
  N-morpholinomethyl-2-phenyl-2-(2-pyrazinyl)thioacetamide
  2-(4-chlorophenyl)-N-morpholinomethyl-2-(2-pyrimidyl)thioacetamide
  N-morpholinomethyl-2-phenyl-2-(2-thiazolyl)thioacetamide
  2-(4,6-dimethyl-2-pyrimidyl)-N-morpholinomethyl-thioacetamide.

EXAMPLE 8

By the procedure of Example 2, using in place of 2-phenyl-2-(2-pyridyl)thioacetamide the following 2-substituted phenyl-2-(2-pyridyl)thioacetamides:

2-(4-chlorophenyl)-2-(2-pyridyl)thioacetamide
2-(2-fluorophenyl)-2-(2-pyridyl)thioacetamide
2-(3-methylphenyl)-2-(2-pyridyl)thioacetamide
2-(4-methoxyphenyl)-2-(2-pyridyl)thioacetamide the products are, respectively:

2-(4-chlorophenyl)-N-morpholinomethyl-2-(2-pyridyl)thioacetamide
2-(2-fluorophenyl)-N-morpholinomethyl-2-(2-pyridyl)thioacetamide
2-(3-methylphenyl)-N-morpholinomethyl-2-(2-pyridyl)thioacetamide
2-(4-methoxyphenyl)-N-morpholinomethyl-2-(2-pyridyl)thioacetamide.

EXAMPLE 9

Methyl 4-thiazolyl ketone (12.7 g.) is added to 3.8 g. of sodium borohydride in 100 ml. of isopropanol and the mixture is heated at reflux for four hours. Dilute hydrochloric acid (100 ml.) is added and the mixture is evaporated to dryness. The residue is dissolved in a small volume of water and the aqueous solution is made basic with 5% aqueous sodium bicarbonate solution, then evaporated to dryness. The residue is extracted with ether and the ether is removed from the extract in vacuo to give α-(4-thiazolyl)ethanol.

A mixture of 8.4 g. of α-(4-thiazolyl)ethanol and 25 ml. of thionyl chloride is heated for 4 hours on a steam bath, then concentrated in vacuo. The residue is dissolved in water and basified with 5 percent aqueous sodium carbonate solution. Extracting with ether, then drying and concentrating the extracts gives 4-(α-chloroethyl)thiazole.

A solution of 7.8 g. of 4-(α-chloroethyl)thiazole is added dropwise to a suspension of 5.2 g. of sodium cyanide in 100 ml. of dimethylsulfoxide. The mixture is heated at 50°C. for 2 hours, then diluted with 150 ml. of a 5 percent aqueous sodium carbonate solution and extracted with ether. The extract is dried and concentrated to give α-(4-thiazolyl)propionitrile.

To 12.4 g. of α-(4-thiazolyl)propionitrile in 13 ml. of pyridine is added 5 ml. of triethylamine. Hydrogen sulfide is bubbled into the mixture for two hours. The mixture is heated in a sealed tube at 100°C. for 15 hours, then cooled and concentrated to dryness. The residue is extracted with chloroform and the extract is concentrated to dryness. The residue is recrystallized from chloroform-hexane to give 2-(4-thiazolyl)thiopropanamide.

Using 2-(4-thiazolyl)thiopropanamide in place of 3-methyl-2-(2-pyridyl)thiobutanamide in the procedure of Example 1, the product is N-morpholinomethyl-2-(4-thiazolyl)-thiopropanamide.

EXAMPLE 10

To a solution of 22.2 g. of methyl magnesium chloride in ether is added 10.5 g. of 4-pyrimidinecarbonitrile in tetrahydrofuran. The resulting mixture is heated at reflux for 24 hours, then poured onto ice. To the mixture is added 75 ml. of 25 percent sulfuric acid. The solution is then made basic with 10 percent aqueous sodium carbonate solution and extracted with ether. The extracts are dried and concentrated to give methyl 4-pyrimidyl ketone.

By the procedure of Example 9, using methyl 4-pyrimidyl ketone in place of methyl 4-thiazolyl ketone, 2-(4-pyrimidyl)thiopropanamide is obtained.

Using 2-(4-pyrimidyl)thiopropanamide in place of 3-methyl-2-(2-pyridyl)thiobutanamide in the procedure of Example 1, the product is N-morpholinomethyl-2-(4-pyrimidyl)thiopropanamide.

EXAMPLE 11

By the procedure of Example 10, using 2-(4-chloropyridine)carbonitrile as the starting material, 2-(4-chloro-2-pyridyl)thiopropanamide is obtained.

Using 2-(4-chloro-2-pyridyl)thiopropanamide in place of 3-methyl-2-(2-pyridyl)thiobutanamide in the procedure of Example 1, the product is N-morpholinomethyl-2-(4-chloro-2-pyridyl)thiopropanamide.

EXAMPLE 12

A solution of 11.8 g. of 2-pyridylacetonitrile in 30 ml. of dimethylsulfoxide is added to a suspension of 2.4 g. of sodium hydride in 50 ml. of dimethylsulfoxide with stirring. The mixture is heated on a steam bath for 2 hours, then cooled to room temperature. 2-Methyl-2-pentenyl-1-chloride (11.8 g.) is added dropwise with stirring. The mixture is heated on the steam bath, with stirring, for 10 hours, then most of the solvent is removed in vacuo. Water is added to the residue, then 200 ml. of ether is added. The ethereal solution is separated from the aqueous layer and rinsed several times with water, then dried, concentrated and distilled to give 4-methyl-2-(2-pyridyl)-4-heptenenitrile.

Treating the above prepared nitrile with hydrogen sulfide by the procedure described in Example 9 gives 4-methyl-2-(2-pyridyl)-4-thioheptenamide.

Using 4-methyl-2-(2-pyridyl)-4-thioheptenamide in place of 3-methyl-2-(2-pyridyl)thiobutanamide in the procedure of Example 1 gives 4-methyl-N-morpholinomethyl-2-(2-pyridyl)-4-thioheptenamide.

EXAMPLE 13

By the procedures described in Example 9, α-(6-methyl-2-pyridyl)-2-propenol is treated with thionyl chloride, the resulting 2-(1-chloro-2-propenyl)-6-methylpyridine is reacted with sodium cyanide and the 2-(6-methyl-2-pyridyl)-3-butenenitrile is treated with hydrogen sulfide to give 2-(6-methyl-2-pyridyl)-3-thiobutenamide.

Reacting 2-(6-methyl-2-pyridyl)-3-thiobutenamide with morpholine and formalin by the procedure of Example 1 gives N-morpholinomethyl-2-(6-methyl-2-pyridyl)-3-thiobuteneamide.

EXAMPLE 14

A solution of 1.66 g. (0.01 mole) of 2-(2-pyridyl)thiopropanamide in 20 ml. of methanol is treated with 1.1 g. (0.015 mole) of morpholine and then with 0.45 g. (0.015 mole) of formaldehyde. The mixture is kept for 48 hours at 25°C., then concentrated in vacuo at 25°C. The residue is dissolved in a minimum of ethanol and treated with a 5 percent solution of oxalic acid in ethanol. Ether is added and the precipitate is filtered off and recrystallized from ethanol to give N-morpholinomethyl-2(2-pyridyl)thiopropanamide oxalate.

The oxalate salt is suspended in water and basified with 5 percent aqueous sodium carbonate solution, then extracted with chloroform. The solvent is evaporated from the extracts and the residue is triturated with hexane. The solid is recrystallized from ether to give N-morpholinomethyl-2-(2-pyridyl)thiopropanamide, m.p. 69°–71°C.

EXAMPLE 15

A solution of 1.0 g. (0.005 mole) of 3-methyl-2-(2-pyridyl)thiobutanamide in 20 ml. of methanol is treated with 0.65 g. (0.0075 mole) of piperidine and then with 0.23 g. of formaldehyde. The mixture is kept for 72 hours at 25°C., then concentrated in vacuo at 25°C. The residue is suspended in water and then extracted into chloroform. The chloroform is evaporated from the extracts and the residue is dissolved in hexane and cooled to −60°C. on a dry ice bath. Upon warming to 25°C., the hexane solution was decanted from insoluble oil and then evaporated in vacuo. The residue is vacuum dried at 0.005 mm. and 25°C. to give 3-methyl-N-piperidinomethyl-2-(2-pyridyl)thiobutanamide.

EXAMPLE 16

A solution of 1.0 g. (0.005 mole) of 3-methyl-2-(2-pyridyl, thiobutanamide in 20 cc. of methanol is treated with 0.54 g. (0.0075 mole) of pyrrolidine and then with 0.23 g. (0.0075 mole) of formaldehyde. The mixture is kept at 25°C. for 72 hours, then worked up as in Example 15 to give, after vacuum drying at 0.005 mm. and 25°C., 3-methyl-N-pyrrolidinomethyl-2-(2-pyridyl)thiobutanamide.

EXAMPLE 17

A solution of 1.94 g. (0.01 mole) of 3-methyl-2-(2-pyridyl)thiobutanamide in 40 ml. of methanol is treated with 1.1 g. (0.015 mole) of diethylamine and 0.45 g. of formaldehyde. The mixture is kept for 48 hours at 25°C., then at 0°C. for 48 hours. The solvent is evaporated and the residue is dissolved in chloroform and washed with water. The solution is dried and the solvent is evaporated off. The residue is vacuum dried at 0.005 mm. and 25°C. for 6 hours to give N-diethylaminomethyl-3-methyl-2-(2-pyridyl)thiobutanamide

EXAMPLE 18

By the procedure of Example 17, using in place of diethylamine, the following di-lower alkylamines:
dimethylamine
dipropylamine
dibutylamine
the products are, respectively:
N-dimethylaminomethyl-3-methyl-2-(2-pyridyl)thiobutanamide
N-dipropylaminomethyl-3-methyl-2-(2-pyridyl)thiobutanamide
N-dibutylaminomethyl-3-methyl-2-(2-pyridyl)thiobutanamide.

EXAMPLE 19

By the procedure of Example 15, using in place of 3-methyl-2-(2-pyridyl)thiobutanamide the following thioamides:
2-(2-pyridyl)thiopropanamide
2-(2-pyrazinyl)thiobutanamide
2-(2-pyridyl)-4-thiopentenamide
the products are, respectively:
N-pyrrolidinomethyl-2-(2-pyridyl)thiopropanamide
N-pyrrolidinomethyl-2-(2-pyrazinyl)thiobutanamide
N-pyrrolidinomethyl-2-(2-pyridyl)-4-thiopeutenamide.

EXAMPLE 20

By the procedure of Example 5, using pyrrolidine in place of morpholine, the product is N-pyrrolidinomethyl-2-(2-pyridyl)thioacetamide.
Similarly, using the following amines:
piperidine
diethylamine
1-methylpiperazine
the products are, respectively:
N-piperidinomethyl-2-(2-pyridyl)thioacetamide
N-diethylaminomethyl-2-(2-pyridyl)thioacetamide
N-(4-methylpiperazinomethyl)-2-(2-pyridyl)thioacetamide.

EXAMPLE 21

By the procedure of Example 5, using pyrrolidine in place of morpholine and the following thioamides in place of 2-(2-pyridyl)thioacetamide:
2-(2-pyrazinyl)thioacetamide
2-(2-quinolyl)thioacetamide
2-(2-pyrrolyl)thioacetamide
2-(4,6-dimethyl-2-pyrimidyl)thioacetamide
2-(4-thiazolyl)thiopropanamide
the products are, respectively:
N-pyrrolidinomethyl-(2-(2-pyrazinyl)thioacetamide
N-pyrrolidinomethyl-2-(2-quinolyl)thioacetamide
N-pyrrolidinomethyl-2-(2-pyrrolyl)thioacetamide
N-pyrrolidinomethyl-2-(4,6-dimethyl-2-pyrimidyl)-thioacetamide
N-pyrrolidinomethyl-2-(4-thiazolyl)thiopropanamide.

EXAMPLE 22

By the procedure of Example 14, 2-benzyl-2-(2-pyridyl)thioacetamide is reacted with morpholine and formaldehyde to give 2-benzyl-N-morpholinomethyl-2-(2-pyridyl)thioacetamide.
By the same procedure, using diethylamine in place of morpholine, the product is 2-benzyl-N-diethylaminomethyl-2-(2-pyridyl)-thioacetamide.
Similarly, using pyrrolidine in place of morpholine, the product is 2-benzyl-N-pyrrolidinomethyl-2-(2-pyridyl)-thioacetamide.

EXAMPLE 23

3-Methyl-N-morpholinomethyl-2-(2-pyridyl)thiobutanamide (500 mg.) in ethanol is treated with ethereal hydrogen chloride to give, after filtering, 3-methyl-N-morpholino-methyl-2-(2-pyridyl)thiobutanamide hydrochloride.
By the same procedure, using etheral hydrogen bromide, the hydrobromide salt is prepared.

EXAMPLE 24

3-Methyl-N-pyrrolidinomethyl-2-(2-pyridyl)thiobutanamide is treated with an equimolar amount of maleic acid in ethanol to give 3-methyl-N-pyrrolidinomethyl-2-(2-pyridyl)thiobutanamide maleate.

EXAMPLE 25

A solution of 1.94 g. (0.01 mole) of 3-methyl-2-(2-pyridyl)thiobutanamide in 40 ml. of methanol is treated with 1.6 g. (0.015 mole) of N-methylaniline and 1.22 ml. of 37 percent formalin solution. The reaction is kept at 25°C. for 12 hours, then refluxed for four hours. The solvents are evaporated in vacuo and the residue is triturated with ethyl acetate and cooled, then filtered. The filtrate is evaporated in vacuo and the resulting oil is triturated with cold ether to give 3-methyl-N-(N-methyl-N-phenylaminomethyl)-2-(2-pyridyl)- thiobutanamide, which after recrystallization from ether melts at 95°–97°C.

By the same procedure using N-ethylaniline in place of N-methylaniline, the product is 3-methyl-N-(N-ethyl-N-phenylaminomethyl)-2-(2-pyridyl)thiobutanamide.

Similarly, using the appropriate N-lower alkylanilines, 3-methyl-N-(N-propyl-N-phenylaminomethyl)-2-(2-pyridyl)thiobutanamide and 3-methyl-N-(N-butyl-N-phenylaminomethyl)-2-(2-pyridyl)thiobutanamide are prepared.

What is claimed is:

1. A compound of the formula:

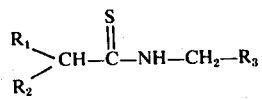

in which:
$R_1$ is 2-quinolyl;
$R_2$ is hydrogen, lower alkyl, lower alkenyl or -$(CH_2)_n$-phenyl;
$R_3$ is di-lower alkylamino, N-lower alkyl-N-phenylamino, pyrrolidino, piperidino or morpholino and
$n$ is 0 or 1 or a pharmaceutically acceptable acid addition salt thereof. -thiazolyl)thiopropanamide.

2. A compound of claim 1 in which $R_2$ is hydrogen or lower alkyl and $R_3$ is morpholino.

3. A compound of claim 1 in which $R_2$ is hydrogen or lower alkyl and $R_3$ is di-lower alkylamino, pyrrolidino, piperidino or morpholino.

4. A compound of claim 1, said compound being N-morpholinomethyl-2-(2-quinolyl)thioacetamide.

5. A compound of claim 1, said compound being N-pyrrolidinomethyl-2-(2-quinolyl)thioacetamide.

* * * * *

UNITED STATES PATENT AND TRADEMARK OFFICE
CERTIFICATE OF CORRECTION

PATENT NO. : 3,931,152
DATED : January 6, 1976
INVENTOR(S) : Henry C. Caldwell and Bernard Loev It is certified that error appears in the above-identified patent and that said Letters Patent are hereby corrected as shown below:

Column 1, line 32, "alkylamine" should read -- alkylamino --.

Column 1, lines 32-33, "phenylamine" should read -- phenylamino -- .

Column 1, line 33, after "piperidino" insert a comma.

Column 2, line 9, "an" should read -- on -- .

Column 7, line 3, "59°-71 C." should read -- 69-71°C. -- .

Column 7, lines 67-68, "thiopeutenamide" should read -- thiopentenamide -- .

Column 10, line 9, delete "-thiazolyl)thiopropanamide." .

Signed and Sealed this thirteenth Day of April 1976

[SEAL]

Attest:

RUTH C. MASON
Attesting Officer

C. MARSHALL DANN
Commissioner of Patents and Trademarks